(12) United States Patent
Kang et al.

(10) Patent No.: US 8,617,546 B2
(45) Date of Patent: Dec. 31, 2013

(54) ANTICANCER AGENT COMPRISING ANTI-PD-1 ANTIBODY OR ANTI-PD-L1 ANTIBODY

(75) Inventors: Chang Yuil Kang, Seoul (KR); Woo Sung Chang, Chungcheongbuk-do (KR); Ji Yeon Kim, Incheon (KR); Dong-Hyeon Kim, Seoul (KR)

(73) Assignee: Seoul National University Industry Foundation, Seoul (KR)

( * ) Notice: Subject to any disclaimer, the term of this patent is extended or adjusted under 35 U.S.C. 154(b) by 0 days.

(21) Appl. No.: 13/398,915

(22) Filed: Feb. 17, 2012

(65) Prior Publication Data

US 2012/0237522 A1 Sep. 20, 2012

Related U.S. Application Data

(63) Continuation of application No. 12/410,732, filed on Mar. 25, 2009, now abandoned.

(30) Foreign Application Priority Data

Oct. 2, 2008 (KR) ........................ 10-2008-0097236

(51) Int. Cl.
*A61K 39/00* (2006.01)
(52) U.S. Cl.
USPC ..................................... 424/130.1; 424/144.1
(58) Field of Classification Search
None
See application file for complete search history.

(56) References Cited

FOREIGN PATENT DOCUMENTS

| JP | 2008-527051 | | 7/2008 |
|---|---|---|---|
| KR | 10-2003-0017733 | | 3/2003 |
| WO | WO 2004/004771 | | 1/2004 |
| WO | WO 2008/085562 | * | 7/2008 |
| WO | WO 2008/085562 A2 | | 7/2008 |

OTHER PUBLICATIONS (FASB Journal, Apr. 2008, 22; abstract lb397, IDS).*
Chang et al (The FASEB Journal, Mar. 2008, 22:106S.13; abstract; IDS).*
Dong-Hyeon Kim et al, 4-1BB Engagement Costimulates NKT Cell Activation and Exacerbates NKT Cell Ligand-Induced Airway Hyperrestponsiveness and Inflammation, The Journal of Immunology, pp. 2062-2068, 2008.
Fumihiko Tsushima et al, Preferential Contribution of B7-H1 to Programmed Death-1-Mediated Regulation of Hapten-Specific Allergic Inflammatory Responses, Eur. J. Immunol. 2003, 33: pp. 2773-2782.
Tomohide Yamazaki et al, Expression of Programmed Death 1 Ligands by Murine T Cells and APC[1], The Journal of Immunology, 2002, 169: pp. 5538-5545.
Tomohide, Yamazaki et al, Blockade of B7-H1 on Macrophages Suppresses CD4[+]T Cell Proliferation by Augmenting IFN-γ-Induced Nitric Oxide Production, The Journal of Immunology, 2005, 175: 1586-1592.
European Search Report, Application No. 09004806.7-1222 dated Nov. 12, 2009.
Parekh et al., Role of the Programmed Death-1 (PD-1) Pathway in Glycolipid Induced iNKT Cell Anergy, The FASB Journal, vol. 22, Abstract Only (Apr. 2008).
Stirnemann et al., Sustained Activation and Tumor Targeting of NKT Cells Using a CD 1 d-anti-HER2-scFv Fusion Protein Induce Antitumor Effects in Mice, J. of Clin. Inv., vol. 118, No. 3, pp. 994-1005 (Mar. 2008).
Molling et al., Invariant Natural Killer T Cells and Immunotherapy of Cancer, Clin. Immun., vol. 129, No. 2, pp. 182-194 (Sep. 9, 2008).
Parekh et al., PD-1/PD-L Blockade Prevents Anergy Induction and Enhances the Anti-Tumor Activities of Glycolipid-Activated Invariant NKT Cells, J. of Immun., vol. 182, No. 5, pp. 2816-2826 (Mar. 5, 2009).
Sullivan et al., Activation or Anergy: NKT Cells are Stunned by α-galactosylceramide, J. of Clin. Inv., vol. 115, No. 9, pp. 2328-2329 (Sep. 2005).
Geng et al., HSP70 Vaccine in Combination with Gene Therapy with Plasmid DNA Encoding sPD-1 Overcomes Immune Resistance and Suppresses the Progression of Pulmonary Metastatic Melanoma, Int. J. of Cancer, vol. 118, No. 11, pp. 2657-2664 (Jun. 1, 2006).
Chang, Woo-Sung et al., Interaction of Programmed Cell Death-1 (PD-1) With Its Ligand PD-Ligand l(PD-L1) Has a Co-Inhibitory Function in NKT Cells, FASB Journal, Mar. 2008, vol. 22, No. 1065.13, Abstract Only.
Chang et al., J. of Immunology, 2008, 181:6707-6710.
Stedman's Medical Dictionary (28th edition, 1 page, printed Nov. 4, 2010).
Montoya et al., Immunology, 2007, 122:1-14.
Exley et al., Eur. J. Immunology, 2008, 38:1756-1766.

* cited by examiner

*Primary Examiner* — Laura B Goddard
(74) *Attorney, Agent, or Firm* — Stein IP, LLC

(57) ABSTRACT

Provided is an anticancer agent which comprises an anti-PD-1 antibody or an anti-PD-L1 antibody as an active ingredient, functioning to reverse the unresponsiveness of iNKT cells in which anergy has been induced by administration with an iNKT cell ligand. The anti-PD-1 or anti-PD-L1 antibody blocks the PD-1/PD-L1-mediated signaling pathway not only to prevent the iNKT cell ligand-induced iNKT cell anergy, but also to reverse the unresponsiveness of already anergic iNKT cells to produce cytokines. In addition, the anti-PD1 or anti-PD-L1 antibody ensures the potent antitumor activity of iNKT cells as demonstrated by a significant reduction in the number of metastatic nodules in B16F10 melanoma metastasis models in vivo. Collectively, the anticancer agent can be very useful in the treatment of cancer, particularly metastatic cancer.

5 Claims, 10 Drawing Sheets

ANTICANCER AGENT COMPRISING ANTI-PD-1 ANTIBODY OR ANTI-PD-L1 ANTIBODY

CROSS-REFERENCE TO RELATED APPLICATIONS

This application is a continuation of U.S. patent application Ser. No. 12/410,732, filed Mar. 25, 2009 now abandoned, which claims priority from Korean Patent Application No. 10-2008-0097236, filed Oct. 2, 2008, the entire disclosures of which are incorporated herein by reference in their entirety.

TECHNICAL FIELD

The present invention relates, in general, to an anticancer agent and, more particularly, to an anticancer agent comprising an anti-PD-1 antibody or an anti-PD-L1 antibody as an active ingredient, functioning to restore the responsiveness of iNKT cells in which anergy has been induced by administration with an iNKT cell ligand.

BACKGROUND OF THE INVENTION

Natural killer T (NKT) cells, co-expressing a T cell receptor and NK cell markers, are essential for several aspects of immunity, such as immunomodulation and immunopotentiation, in various immune diseases including autoimmune diseases, infectious diseases, cancer, etc. NKT cells exist at high levels in the thymus, the liver, and the bone marrow, but at low levels in the spleen, lymph nodes and blood.

Unlike conventional T cells that recognize small peptide antigens presented by major histocompatibility complex MHC class 1 or MHC class 2, NKT cells recognize glycolipid antigens presented by CD1d, a MHC class 1-like molecule. A major subset of NKT cells, called type 1 NKT cells or invariant natural T (iNKT) cells, express an invariant natural T cell receptor (TCR) composed of Vα14-Jα18 chains in mice (Vα24-Jα18 in humans). Upon TCR stimulation with a ligand, such as α-galactosylceramide (α-GC), iNKT cells rapidly produce a wide range of cytokines including IL-4, IFN-γ, L-12, and GM-CSF. This rapid and potent response to a ligand enables iNKT cells to enhance or regulate the activity of various immune cells in innate and acquired immunity. Found in diverse diseases and promoting tumor rejection or regulating autoimmune disorders, these immunomodulatory roles of iNKT cells are studied for use in immunotherapy treatments for cancer and autoimmune diseases.

However, iNKT cells tend to greatly decrease in responsiveness following repeated stimulation after a first stimulation with their ligands via the T cell receptor. For instance, iNKT cells that have been stimulated in vivo with a-GC have reduced proliferation and cytokine production upon secondary stimulation with the same ligand. This iNKT cell anergy is a major obstacle in immunotherapeutic trials targeting iNKT cells.

Conventional T cells are known to become anergic when they receive a TCR signal with insufficient co-stimulatory signals. Co-stimulatory molecules such as CD28, CD40L and ICOS are known to be involved in the development and activation of iNKT cells. Recently, it has been reported that 4-1BB contributes to promote the activation of iNKT cells as a co-stimulatory molecule and can affect iNKT cell-mediated allergic lung inflammation (Kim, D. H., W. S. Chang, Y. S. Lee, K. A. Lee, Y. K. Kim, B. S. Kwon, and C. Y. Kang. 2008. 4-1BB engagement co-stimulates NKT cell activation and exacerbates NKT cell ligand-induced airway hyperresponsiveness and inflammation. J Immunol 180:2062-2068.). On the other hand, it has recently been suggested that coinhibitory molecules, such as PD-1, B7H3, and B7H4, may actively anergize or tolerize T cells by delivering inhibitory signals into TCR-stimulated T cells. In a lymphocytic choriomeningitis virus (LCMV) infected model, CD8 T cells are tolerized by LCMV epitope-presenting dendritic cells. However, the blockade of the PD-1 signal can reverse the anergic phenotype of CD8 T cells. It has also been reported that the inhibition of PD-1/PD-L1 restores the function of exhausted CD8 T cells in a chronic infection model.

Programmed death-1 (PD-1) is a 55 KDa type 1 transmembrane protein of the immunoglobulin superfamily, and is known as a co-inhibitory molecule on T cells. That is, PD-1 is a member of the co-inhibitory molecules of the CD28 family (e.g., CD28, CTLA4, ICOS and BTLA) expressed on activated B cells, T cells and bone marrow cells. Two ligands for PD-1, PD-L1 and PD-L2, have been identified thus far. The interaction of PD-1 with the PD ligands can transduce inhibitory or co-stimulatory signals into the T cells. In conventional T cells, PD-1 is not expressed on naive T cells, but is inducibly expressed after T cell activation. As for PD-L1, it is expressed to some degree on naive T cells and its level is increased on activated T cells. PD-L1 is found at high levels in various human cancers and interacts with PD-1 to transduce inhibitory or co-stimulatory signals from entering into the T cells. For example, the interaction between PD-1 and PD-L1 induces a decrease in the level of tumor invasive lymphocytes and in T cell receptor-mediated proliferation and causes the immune evasion of tumor cells. In PD-1-deficient animals, PD-1 develops various autoimmune phenotypes, such as autoimmune cardiac infarction and lupus-like syndromes with arthritis and nephritis, and plays an important role in the development of autoimmune encephalomyelitis, systemic lupus erythematosus, graft-versus-host disease (GVHD), type 1 diabetes and rheumatic arthritis. Aged PD-1-deficient mice develop autoimmune diseases, indicating that PD-1 plays a critical role in the regulation of autoimmunity and immune tolerance. In particular, PD-1 signals are essential for inducing T cell exhaustion during chronic infection.

With the ability thereof to stimulate the T cell receptor to rapidly produce various cytokines of iNKT cells, the NKT cell ligand α-GC has conventionally been used as an anticancer agent. However, since repeated stimulation of iNKT cells with α-GC induces anergy leading to a great decrease in responsiveness, it cannot achieve effective anticancer effects. Therefore, there is a pressing need for an anticancer agent that can restore the responsiveness of iNKT cells even in the state of anergy caused by stimulation with iNKT cell ligands.

Leading to the present invention, intensive and thorough research into an anticancer agent taking advantage of the responsiveness of iNKT cells, conducted by the present inventors, resulted in the finding that PD-1 expressed on iNKT cells is upregulated after stimulation and that blocking of the PD-1/PD-L1 signaling pathway by an anti-PD-1 or anti-PD-L1 antibody allows iNKT cells under an iNKT cell ligand-induced anergy condition to recover their responsiveness, such as the production of cytokines. Also, the anti-PD1 or anti-PD-L1 antibody was found to induce potent antitumor activity of iNKT cells as demonstrated by a significant reduction in the number of metastatic nodules in B16F10 melanoma metastasis models in vivo.

SUMMARY OF THE INVENTION

It is therefore an object of the present invention to provide an anticancer agent which is based on the activity of iNKT cells, featuring the recovery of iNKT cell responsiveness.

It is another object of the present invention to provide a method for the treatment of cancer using the same.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE EMBODIMENTS

Figure 1:
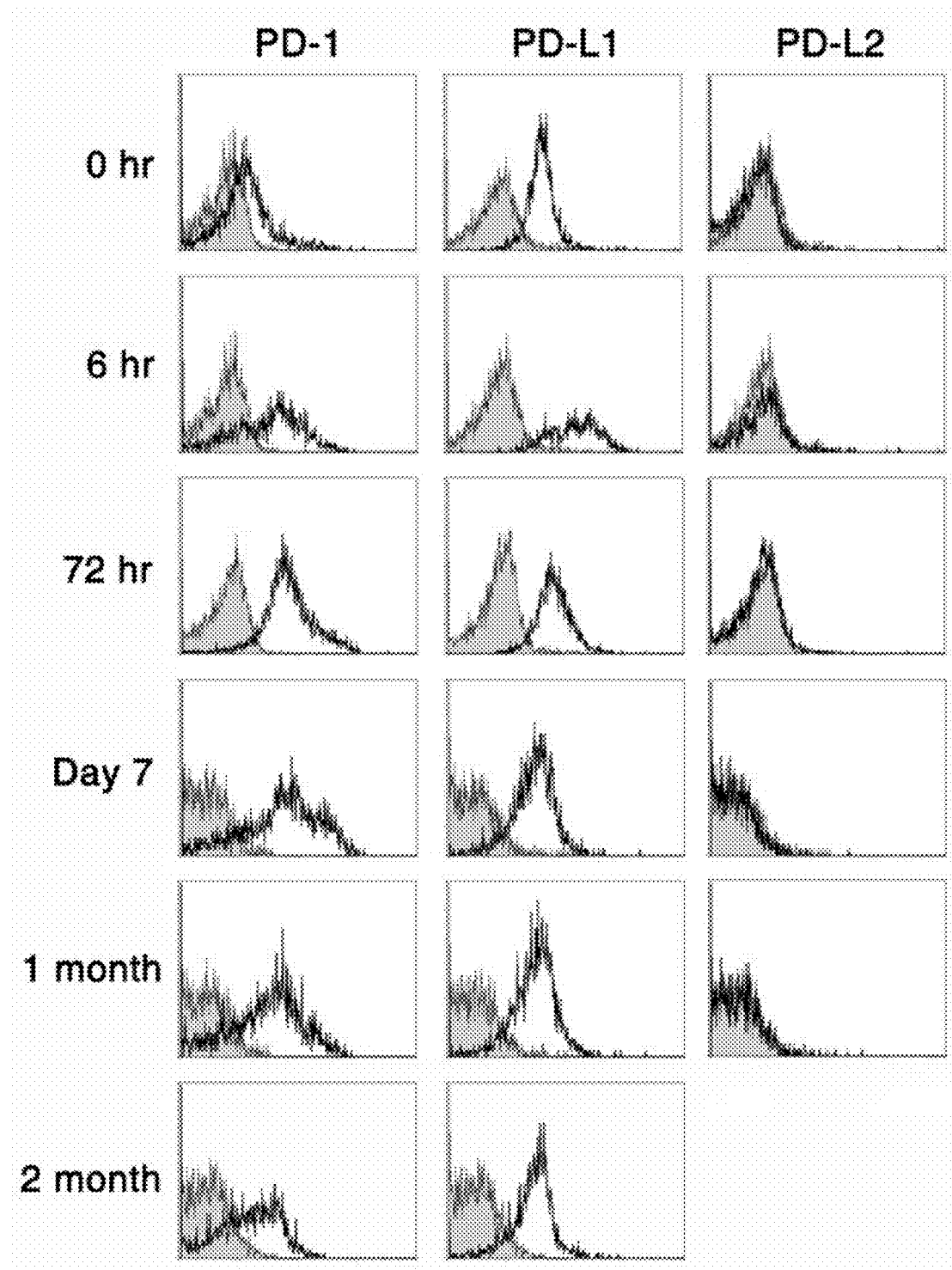
FIG. 1 is of flow histograms showing the expression levels of PD-1. PD-L1 and PD-L2 on iNKT cells of the splenocytes isolated from α-GC-treated C57BL/6 mice at indicated time points (0 hr, 6 hrs, 72 hrs, 7 days, 1 month and 2 months) after treatment.

Reference will now be made in detail to the present embodiments of the present invention, examples of which are illustrated in the accompanying drawings, wherein like reference numerals refer to the like elements throughout. The embodiments are described below in order to explain the present invention by referring to the figures.

In accordance with an aspect thereof, the present invention provides an anticancer agent, comprising an iNKT cell ligand as a first anticancer factor and an anti-PD-1 antibody or anti-PD-L1 antibody as a second anticancer factor, having a function of reversing unresponsiveness of iNKT cells in which anergy is induced by administration with the iNKT cell ligand.

In accordance with another aspect thereof, the present invention provides a method for reversing the unresponsiveness of iNKT cells with anergy induced therein by iNKT cell ligand treatment, comprising treating the anergic iNKT cells with an anti-PD-1 antibody or an anti-PD-L1 antibody.

The iNKT cell ligand may be selected from a group consisting of alpha-galactosyl ceramide, alpha-glucuronosyl ceramide, phosphatidylinositoltetramannoside, isoglobotrihexosylceramide, ganglioside GD3, phsphatidylcholine, phosphatidylethanolamine, phosphatidylinositol, sulfatide, beta-galactosylceramide, lipophosphoglycan, glycoinositol phospholipid, alpha-galactosylceramide analogs including beta-anomer galactoceramide and alpha-anomer galactosylceramide, and bacterial lipid antigens.

The anti-PD-1 antibody or the anti-PD-L1 antibody may be a monoclonal antibody or a polyclonal antibody.

The anti-PD-1 antibody or anti-PD-L1 antibody according to the present invention can block the signaling of PD-1 or PD-L1 to prevent the iNKT cell ligand-induced anergy of iNKT cells and can provide cytokine secretion ability for even anergic iNKT cells to restore their responsiveness. In addition, the anti-PD-1 antibody or anti-PD-L1 antibody of the present invention inhibits the anergy induction of iNKT cells to significantly decrease the number of pulmonary nodules in a lung metastasis model of B16F10 melanoma, thus effectively eliciting anticancer immune responses of iNKT cells and showing anti-tumor effects of iNKT cells against cancer metastasis. Therefore, an anticancer agent comprising the anti-PD-1 antibody or anti-PD-L1 antibody of the present invention can be very useful in the treatment of cancer, particularly, metastatic cancer.

The cancer to which the anticancer agent according to the present invention is therapeutically applicable may be gynecologic tumor, endocrine gland cancer, CNS (central nervous system) tumor or ureter cancer. Concrete examples of the cancer include lung cancer, stomach cancer, liver cancer, bone cancer, pancreatic cancer, skin cancer, head and neck cancer, melanoma, uterine cancer, ovarian cancer, rectal cancer, colorectal cancer, colon cancer, breast cancer, uterine sarcoma, Fallopian tube carcinoma, endometrial carcinoma, uterine cervical carcinoma, vaginal carcinoma, vulva carcinoma, esophageal cancer, larynx cancer, small intestine cancer, thyroid cancer, parathyroid cancer, soft tissue sarcoma, uterine cancer, penis cancer, prostate cancer, chronic or acute leukemia, pediatric solid tumor, differentiated lymphoma, bladder cancer, kidney cancer, renal cell carcinoma, renal pelvic carcinoma, primary CNS lymphoma, spinal cord tumor, brainstem glioma, and pituitary adenoma.

The anticancer agent of the present invention may be formulated into a pharmaceutical composition with at least one conventional anticancer ingredient.

In addition to the active ingredients, the pharmaceutical composition may further comprise a pharmaceutically acceptable carrier. Examples of the pharmaceutically acceptable carrier include saline, sterile water, Ringer's solution, buffered saline, dextrose solution, maltodextrin solution, glycerol, ethanol, etc. Optionally, conventional additives, such as antioxidants, buffers, bacteriostatic agents, etc., may be added to the composition. For the preparation of dosage forms including injections, such as aqueous solutions, suspensions and emulsions, pills, capsules, granules and tablets, the active ingredients may be admixed with a diluent, a dispersant, a surfactant, a binder and/or a lubricant. Reference may be made to literature (Remington's Pharmaceutical Science (recent edition), Mack Publishing Company, Easton Pa.) upon the formulation of the pharmaceutical composition into suitable dosage forms.

The composition of the present invention may be administered via oral routes or parenteral routes (e.g., intravenous, subcutaneous, intraperitoneal, topical, etc.). The effective dosage of the anticancer agent in accordance with the present invention depends on various factors, including the patient's weight, age, gender, state of health, diet, the time of administration, route of administration, excretion rate, severity of diseases, etc. In general, it may be administered in a single dose, and preferably in multiple doses per day at a daily dose ranging from 0.01 to 1000 mg/day, and preferably from 0.1 to 100 mg/kg of the anti-PD-1 antibody or anti-PD-L1 antibody.

For the effective prophylaxis and treatment of cancer, the composition according to the present invention may be used alone or in combination with surgical operation, hormonal therapy, chemotherapy, and/or biological response controllers.

A better understanding of the present invention may be obtained through the following examples which are set forth to illustrate, but are not to be construed as limiting the present invention.

EXAMPLES

Example 1

Expression of PD-1 and PD Ligands in iNKT Cells

1. Experimental Animals

Six- to eight-week-old female C56BL/6 mice were purchased from Orient Bio. All mice were bred and maintained in specific pathogen-free conditions.

2. Reagents and Antibodies alpha.-GC was dissolved in PBS containing 0.5% Tween 20. Hybridoma clones producing antibodies to mouse PD-1 (RMP1-14, rat IgG2a), PD-L1 (MIH-5, rat IgG2a), and PD-L2 (Ty25, rat IgG2a) were produced according to methods well known in the art [Yamazaki, T., H. Akiba, H. Iwai, H. Matsuda, M. Aoki, Y. Tanno, T. Shin, H. Tsuchiya, D. M. Pardoll, K. Okumura, M. Azuma, and H. Yagita. 2002. Expression of programmed death 1 ligands by murine T cells and APC. J Immunol 169:5538-5545.; Tsushima, F., H. Iwai, N. Otsuki, M. Abe, S. Hirose, T. Yamazaki, H. Akiba, H. Yagita, Y. Takahashi, K. Omura, K. Okumura, and M. Azuma. 2003. Preferential contribution of B7-H1 to programmed death-1-mediated regulation of hapten-specific allergic inflammatory responses. Eur J Immunol 33:2773-2782.; Yamazaki, T., H. Akiba, A. Koyanagi, M. Azuma, H. Yagita, and K. Okumura. 2005. Blockade of B7-H1 on macrophages suppresses CD4+ T cell proliferation by augmenting IFN-gamma-induced nitric oxide production. J Immunol 175: 1586-1592.]. All clones were cultured in RPMI 1640 (Gibco) with 10% FBS (Gibco) and 1% penicillin/streptomycin (Bio-Whittaker). All antibodies were prepared from the ascites of nude mice using caprylic acid purification. Control rat IgG was also prepared by caprylic acid purification from sera of naive rats.

3. Expression of PD-1 and PD Ligands on iNKT Cells after α-GC Administration

Splenocytes were isolated from C57BL/6 mice administered with 2 μg of α-GC at different time points (0 hr, 6 hrs, 72 hrs, 7 days, one month and two months) after the administration. The cells were stained with a PE-conjugated anti-PD-1 monoclonal antibody, a PE-conjugated anti-PD-L1 monoclonal antibody, a PE-conjugated anti-PD-L2 monoclonal antibody and a PE-conjugated isotype control monoclonal antibody, respectively. iNKT cells were gated on B220⁻ TCR-$\beta^{int}$α-GC/CD1d:Ig⁺ population. PD-1, PD-L1 and PD-L2 expression (open histograms) was analyzed by FACS. The results are given in FIG. 1. Shaded histograms indicate staining with isotype control niAbs.

As depicted in FIG. 1, PD-1 was constitutively expressed on iNKT cells at a low level and its expression was upregulated after α-GC stimulation, followed by the persistence of the upregulated level for two months. On the other hand, PD-L1 expression was temporarily increased on α-GC-stimulated iNKT cells but declined toward naive state levels within 72 hrs. As for PD-L2, its expression was not found on iNKT cells regardless of their activation status.

Example 2

Effects of PD-1, PD-L1 and PD-L2 on iNKT Cell Activation

The following in vitro and in vivo experiments were conducted to examine the effects of PD-1, PD-L1 and PD-L2 on iNKT cell activation.

1. iNKT Cell Activation In Vitro

After being prepared from naive C57BL/6 mice, 5×10⁵ splenocytes were incubated for 3 days with 100 ng/ml of α-GC in the presence of 50 μg/ml of the control rat IgG, the anti-PD-1 mAb, the anti-PD-L1 mAb, or the anti-PD-L2 mAb. Then, the supernatants were obtained and assayed for IFN-γ and IL-4 levels by ELISA.

Figure 2:
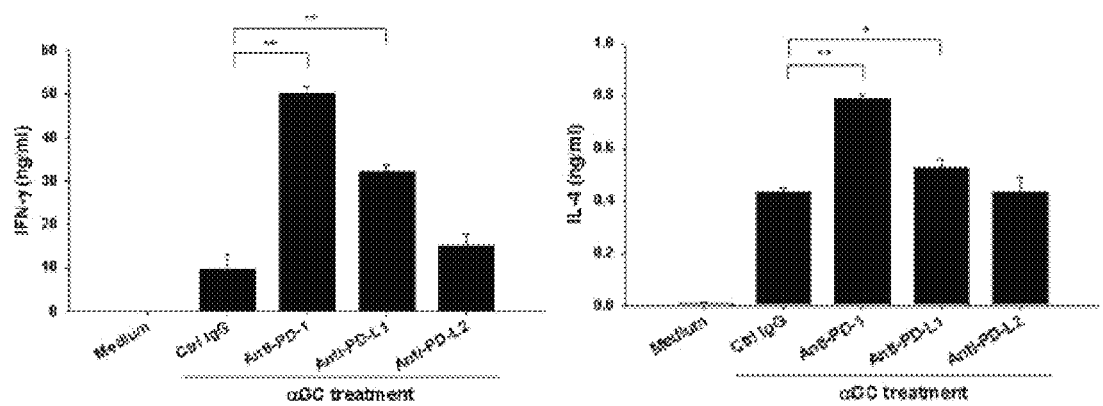
FIG. 2 is of histograms showing IFN-γ and IL-4 levels in the supernatants obtained after incubating splenocytes isolated from naive C57BL/6 mice with α-GC in the presence of control rat IgG, anti-PD-1 monoclonal antibody, anti-PD-L1 monoclonal antibody or anti-PD-L2 monoclonal antibody as analyzed by ELISA (in vitro).

The results are given in FIG. 2.

Compared with control IgG treatment, as is apparent from FIG. 2, anti-PD-1 mAb significantly increased the production of IFN-γ and, to a lesser extent, IL-4. Anti-PD-L1 mAb also induced greater production of IFN-γ, but anti-PD-L2 mAb did not.

2. iNKT Cell Activation In Vivo

C57BL/6 mice was injected with 200 μg of the control rat IgG, the anti-PD-1 mAb, the anti-PD-L1 mAb or the anti-PD-L2 mAb 24 hrs before treatment with 2 μg of α-GC. Sera were obtained at 0, 2, 6, 12, 24, 48 and 72 hrs after the treatment, followed by ELISA analysis for IFN-γ and IL-4 levels.

In order to determine whether the increased production of IFN-γ was distinctively attributed to iNKT cells, intracellular cytokine staining was followed by flow cytometry analysis. In this regard, splenocytes were isolated 2 hrs after α-GC treatment and 5×10⁶ cells were incubated with Golgi plug for 2 hrs to accumulate cytokines. Intracellular cytokine staining was performed using BD Cytofix/Cytoperm Plus with Golgiplug kit according to the manufacturer's protocol (BD Biosciences). iNKT cells were gated on B220⁻TCR-β$^{int}$ α-GC/CD1d:Ig⁺ population and IFN-γ⁺ or IL-4⁺ iNKT cells were analyzed by flow cytometry.

Figure 3:
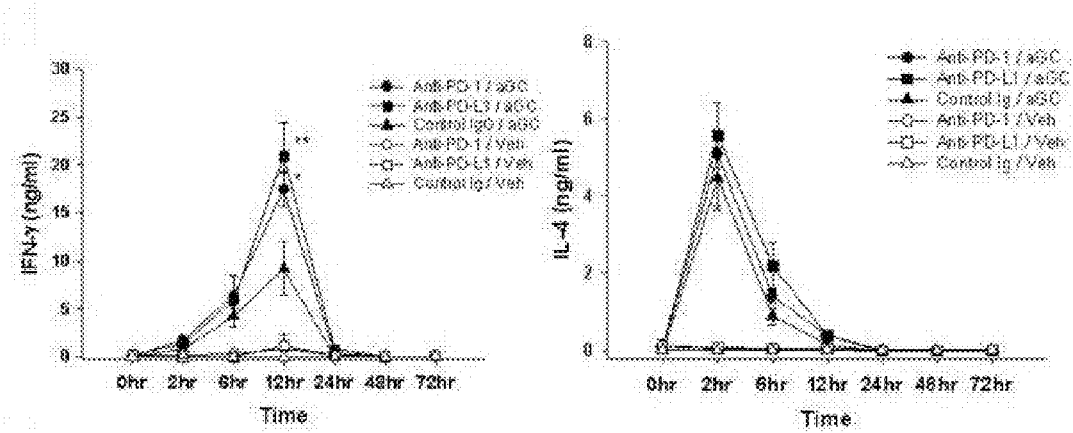
FIG. 3 is of plots showing IFN-γ and IL-4 levels in the sera obtained from the C57BL/6 mice, which were intraperitoneally injected with control rat IgG, anti-PD-1 monoclonal antibody, anti-PD-L1 monoclonal antibody or anti-PD-L2 monoclonal antibody 24 hrs before α-GC treatment, at 0, 2, 6, 12, 24, 48 and 72 hrs after the α-GC treatment as analyzed by ELISA (in vivo).
Figure 4:
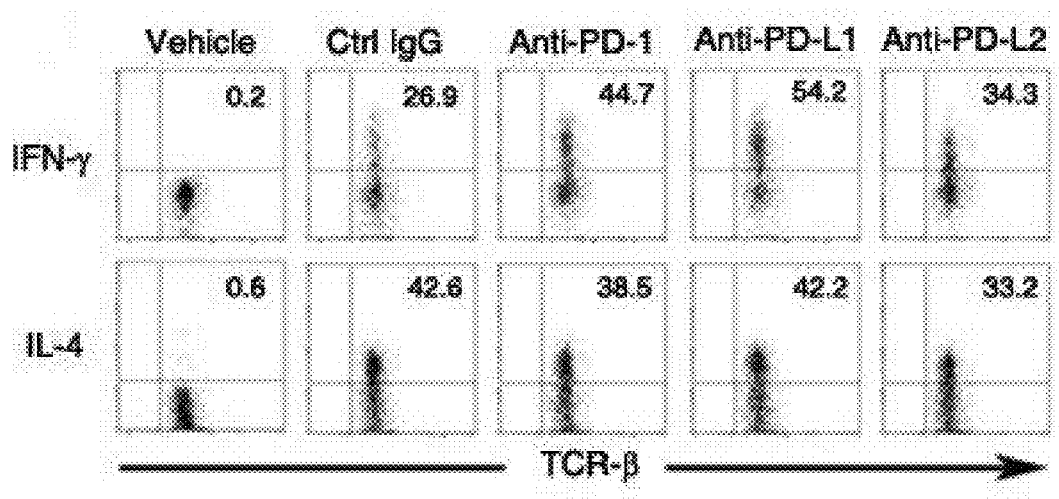
FIG. 4 shows FACS results of IFN-γ$^+$ or IL-4$^+$ iNKT cells on which intracellular cytokine staining was performed to examine if the increased production of IFN-γ and IL-4 in the sera of FIG. 3 comes from iNKT cells.

IFN-γ and IL-4 levels in blood are depicted in FIG. 3 and flow histograms of IFN-γ⁺ and IL-4⁺ iNKT cells are given in FIG. 4.

As shown in FIG. 3, the blood IFN-γ and IL-4 levels were observed to peak, respectively, within 12 hrs and 2 hrs after α-GC treatment, indicating iNKT cell activation. IFN-γ levels in the sera of anti-PD-1 or anti-PD-L1 mAb-treated mice were significantly enhanced compared with levels in the group treated with control IgG. Slightly different L-4 production was observed after treatment with the blocking Abs, but with no significance.

As shown in FIG. 4, iNKT cells producing IFN-γ increased in number because they blocked PD-1/PD-L1 interaction with the anti-PD-1 mAb or anti-PD-L1 mAb in comparison with control cells. On the other hand, no significant differences were found between populations of IL-4⁺ iNKT cells and control cells after mAb treatment. These data indicate that the blockage of PD-1/PD-L1 interaction allows the delivery of the co-inhibitory signal during iNKT activation, resulting in increased IFN-γ secretion from iNKT cells.

Example 3

Effects of Blockage of PD-1/PD-L1 Interaction on Responsiveness of Anergic iNKT Cells The following in vitro and in vivo experiments were performed in order to examine whether the blockage of PD-1/PD-L1 interaction reverses iNKT cell anergy.

1. Recovery of Responsiveness of Anergic iNKT Cells In Vitro

The α-GC-induced unresponsiveness of iNKT cells was detected as early as 3 days after primary stimulation and observed to persist until 7.about.30 days after α-GC stimulation. Thus, C57BL/6 mice were injected with 2 μg of α-GC to induce iNKT cell anergy. One week and one month later, splenocytes were isolated from the mice and 5×10⁵ cells were incubated for 3 days with 100 ng/ml of α-GC in the presence of 50 μg/ml of the control rat IgG, the anti-PD-1 mAb, the anti-PD-L1 mAb, or the anti-PD-L2 mAb. Also, splenocytes isolated from the mice were incubated for 3 days with 10 ng/ml of α-GC without mAb, and these were represented by 'activation'. The supernatants were then assayed for IFN-γ and IL-4 levels by ELISA [*:p<0.05 and **:p<0.01 (vs. control rat IgG)].

Figure 5:
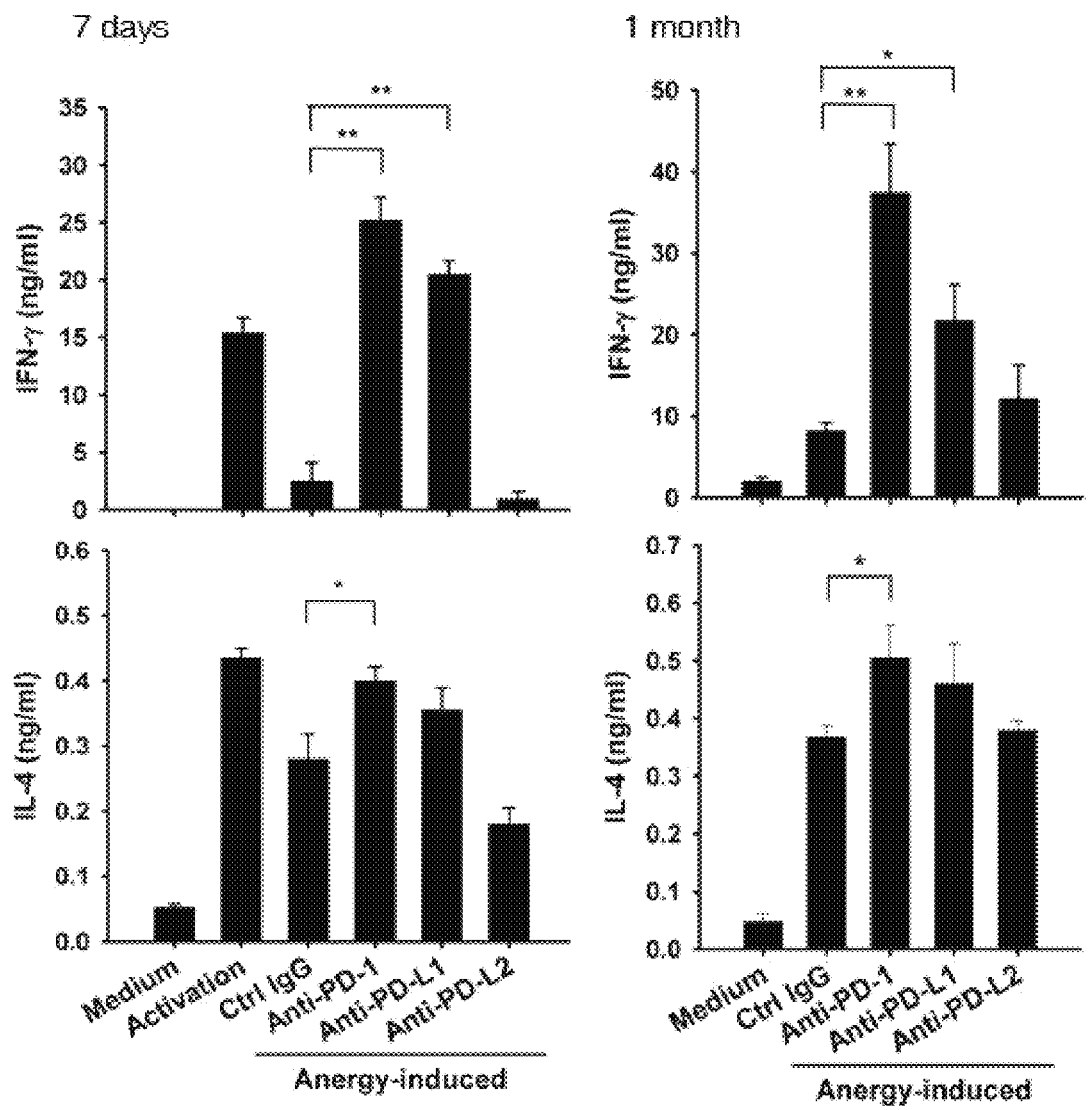
FIG. 5 is of histograms showing IFN-γ and IL-4 levels in the supernatants obtained after the splenocytes of C57BL/6 mice, in which iNKT cell anergy was induced by α-GC treatment 7 days and one month before splenocyte isolation therefrom, were incubated with α-GC in the presence of control rat IgG, anti-PD-1 monoclonal antibody, anti-PD-L1 monoclonal antibody or anti-PD-L2 monoclonal antibody, as analyzed by ELISA (in vitro).

The results are depicted in FIG. 5.

As seen in the graphs of FIG. 5, when restimulated with α-GC in the presence of the control IgG, the splenocytes of the mice in which iNKT cell anergy was induced by pretreatment with α-GC 7 days before the restimulation were found to greatly decrease in the production of IFN-γ and IL-4. In contrast, the restimulation of iNKT cell anergy-induced splenocytes with α-GC in the presence of the anti-PD-1 antibody or anti-PD-L1 antibody resulted in a great increase in the production of IFN-γ and L-4 (A). This upregulation was observed to persist for one to two months after α-GC treatment (B). Therefore, the blockage of PD-1/PD-L1 interaction during restimulation with α-GC reverses the established anergic phenotype of iNKT cells.

2. Recovery of Responsiveness of Anergic iNKT Cells In Vivo

200 μg of the control rat IgG, the anti-PD-1 antibody or the anti-PD-L1 antibody was intraperitoneally injected into C57BL/6 mice 24 hrs before treatment with 2 μg of α-GC. 14 days later, 2 μg of α-GC was injected again, followed by the preparation of sera 2 and 12 hrs after the re-injection for ELISA assay of IL-4 and IFN-γ levels, respectively.

Splenocytes (5×10⁶ cells), prepared two and twelve hours after the second injection of α-GC, were incubated with Golgi plug for 2 hrs to accumulate cytokines. Intracellular cytokine staining was performed on the splenocytes prepared 2 hrs after the secondary GC treatment, using BD Cytofix/Cytoperm Plus with Golgiplug kit according to the manufacturer's protocol (BD Biosciences). The splenocytes prepared 12 hrs later were used in an assay for CD69 expression in iNKT and NK cells. iNKT cells were gated on B220⁻TCR-β$^{int}$α-GC/CD1d:1g⁺ population and NK cells were gated on B220⁻TCR-β⁻NK1.1$^{high}$ population. IFN-γ⁺ or IL-4⁺ iNKT cells were analyzed by flow cytometry. Also, CD69 expression on iNKT and NK cells was analyzed by flow cytometry.

Figure 6:
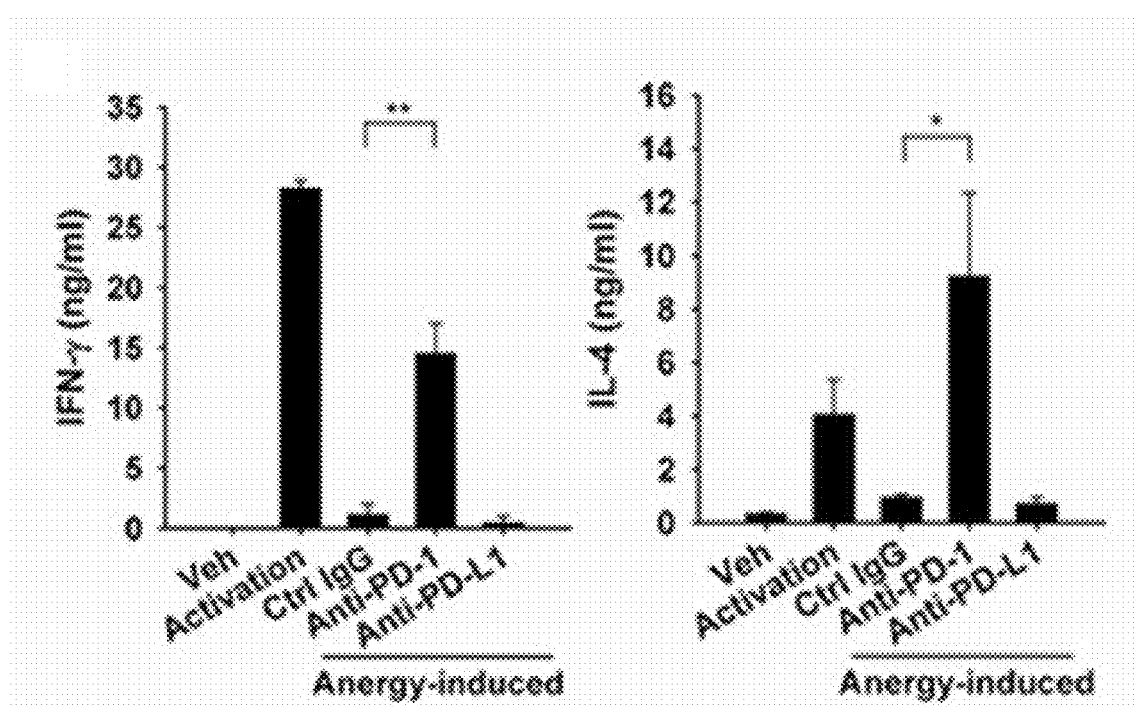
FIG. 6 is of histograms showing IFN-γ and L-4 levels in sera from C57BL/6 mice, as analyzed by ELISA. The mice were intraperitoneally injected with control rat IgG, anti-PD-1 monoclonal antibody, anti-PD-L1 monoclonal antibody or anti-PD-L2 monoclonal antibody, followed by double injection with α-GC 24 hrs and 14 days later. The sera were obtained 2 and 12 hrs after the secondary injection of α-GC (in vivo).
Figure 7:
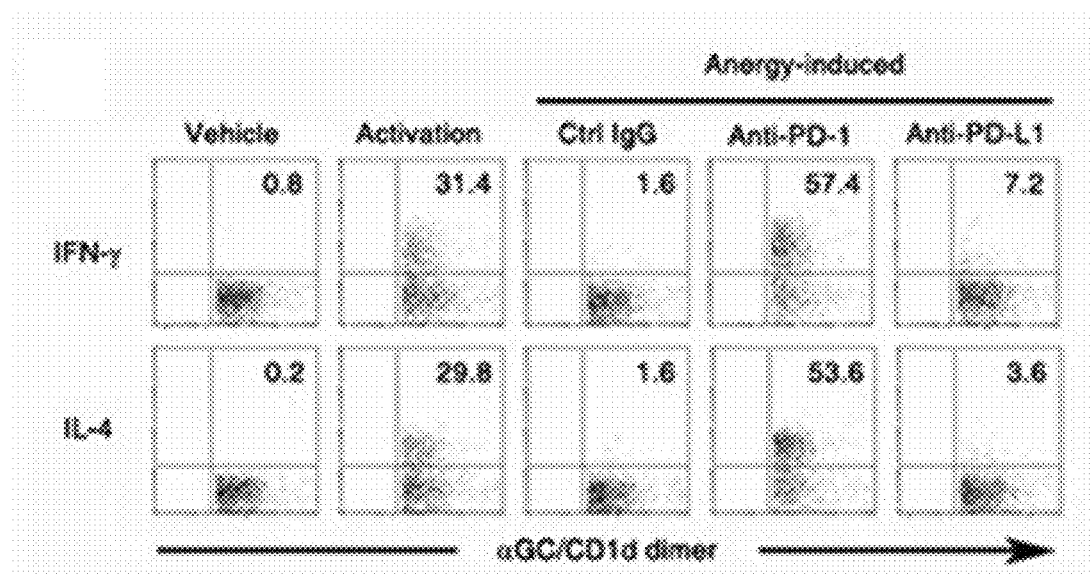
FIG. 7 shows FACS results of IFN-γ$^+$ or IL-4$^+$ iNKT cells after intracellular cytokine staining was performed on the splenocytes isolated 2 hrs after the secondary injection (in vivo).
Figure 8:
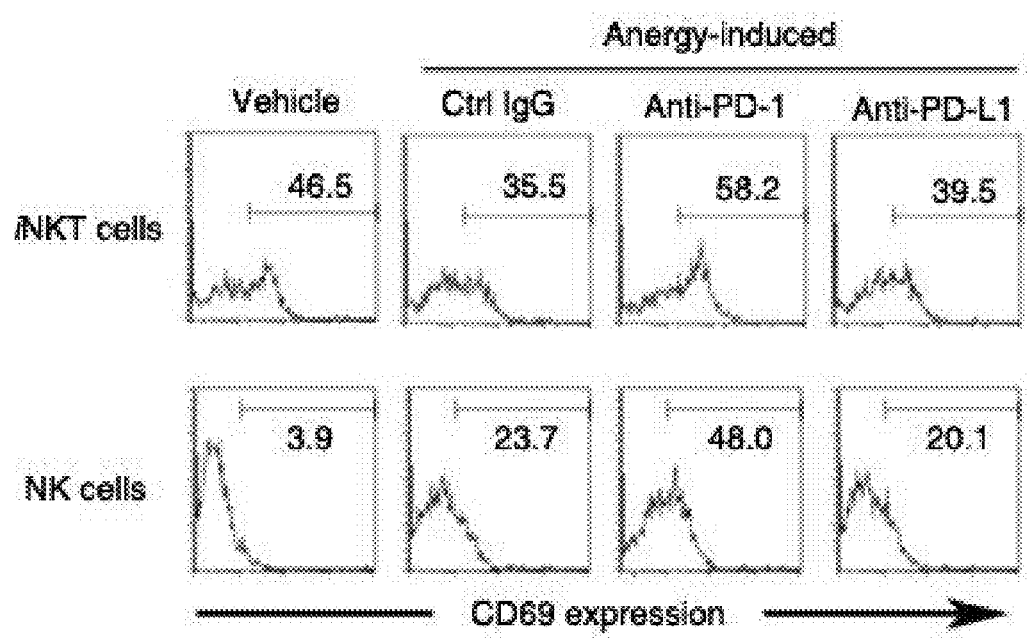
FIG. 8 shows CD69 expression levels on iNKT and NK cells as measured by flow cytometry using the splenocytes isolated 12 hrs after the secondary injection (in vivo).

IFN-γ and L-4 levels in blood are graphed in FIG. 6 and FACS results of IFN-γ⁺ or L-4⁺ iNKT cells and flow histograms of CD69 expression on iNKT and NK cells are given in FIGS. 7 and 8, respectively.

Like mice treated with control rat IgG, as seen in FIG. 6, mice pretreated with α-GC produced significantly low IFN-γ and L-4 upon secondary α-GC injection. In contrast, mice treated with the anti-PD-1 antibody during the primary α-GC injection produced remarkably higher IFN-γ and L-4 upon the secondary α-GC injection than did the control IgG-treated group.

As seen in FIG. 7, the increased cytokine production was attributed to iNKT cells.

It was also found that CD69 expression upon secondary α-GC injection was increased on iNKT and NK cells in a similar manner by the treatment with anti-PD-1 mAbs, as shown in FIG. 8. Thus, PD-1/PD-L1 interaction is essential for the induction of iNKT cell anergy in vivo.

Example 4

Effects of Anti-PD-1 mAb or Anti-PD-L1 mAb on Anti-Tumor Activity of Activated iNKT Cells The following experiments were performed to investigate the effects of the anti-PD-1 antibody or the anti-PD-L1 antibody on the anticancer activity of activated iNKT cells in a B16F10 melanoma metastasis model.

1. Weight of Lung

Skin tumor cells (B16F10, ATCC) were cultured in DMEM media supplemented with 10% FBS and 1% penicillin/streptomycin. C56BL/6 mice were intraperitoneally injected with 200 g of the control rat IgG, the anti-PD-1 mAb or the anti-PD-L1 mAb 24 hrs before i.v. inoculation with 2×10⁵ tumor cells. On Days zero, 4 and 8, the mice were treated with 500 ng of α-GC plus 200 μg of the control rat IgG, the anti-PD-1 mAb or the anti-PD-L1 mAb. On Day 14, the lungs were weighed and weight differences between metastatic and normal lungs are graphed in FIG. 9.

Figure 9:
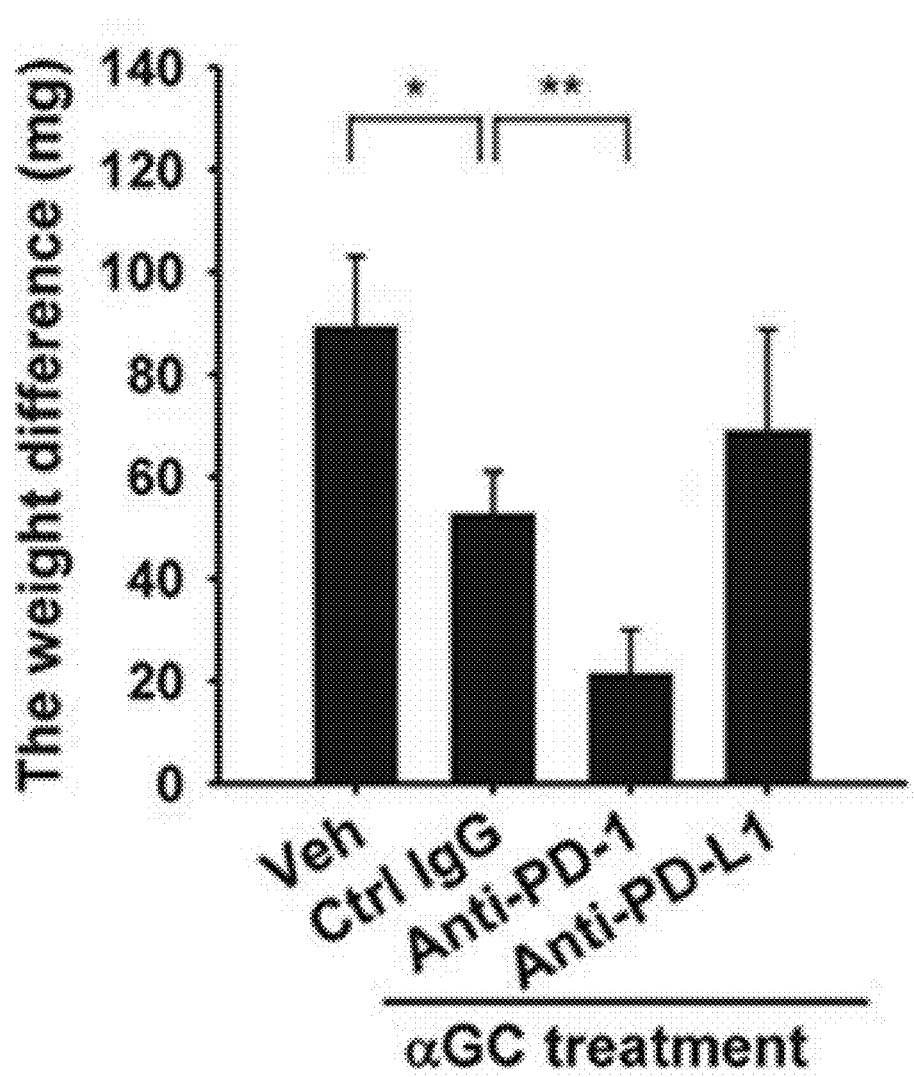
FIG. 9 is a histogram showing weights of normal and metastatic lungs of C57BL/6 mice. The mice were intraperitoneally injected with control rat IgG, anti-PD-1 monoclonal antibody or anti-PD-L1 antibody 24 hrs before intravenous injection with skin tumor cells. On Days 0, 4 and 8, the mice were co-administered with α-GC and the control rat IgG, the anti-PD-1 antibody or the anti-PD-L1 antibody. The lungs were excised 14 days after the co-administration.

As depicted in FIG. 9, the B16F10 metastatic lungs from the group treated with α-GC plus the anti-PD-1 mAb were significantly reduced in weight compared with those from the group treated with α-GC plus the control rat IgG.

2. Number of Pulmonary Nodules

Anergy-induced iNKT cells were assayed for the recovery of anti-tumor activity by the antibodies of the present invention. In this regard, naive C57BL/6 mice were intraperitoneally injected with 200 μg of the control rat IgG, the anti-PD-1 antibody or the anti-PD-L1 antibody 24 hrs after which injection with 2 μg of α-GC induced iNKT cell anergy. 7 days later, $5\times10^5$ B16F10 tumor cells were i.v. injected. On Day 0, 4 and 8, the mice were treated with 500 ng of α-GC to induce anti-tumor activity of iNKT cells. 14 days later, the lungs were excised and the nodules formed by cancer metastasis were counted (A). The isolated lungs were observed under an optical microscope (B). The results are given in FIG. 10.

Figure 10A:
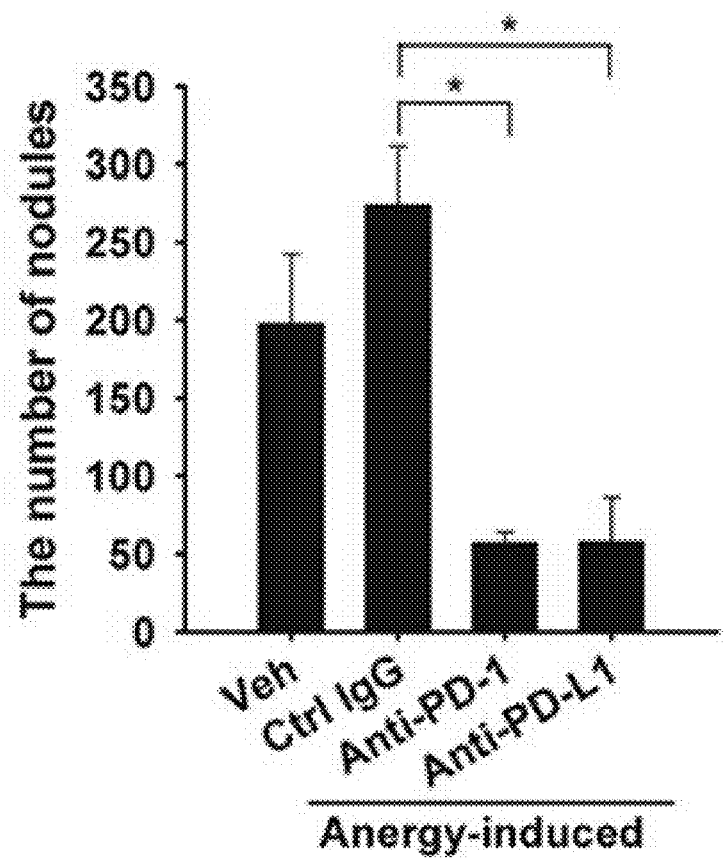
FIG. 10 shows effects of the blockage of PD-1/PD-L1 interaction on the antitumor activity of iNKT cells in terms of the number of metastatic pulmonary nodules (A) and optical microscopic views (B). C57BL/6 mice were intraperitoneally injected with control rat IgG, anti-PD-1 antibody or anti-PD-L1 antibody 24 hrs before α-GC treatment. 7 days later, the mice were intravenously injected with skin tumor cells and re-injected with α-GC on Days 0, 4 and 8. 14 days later, the lungs were excised.
Figure 10B:
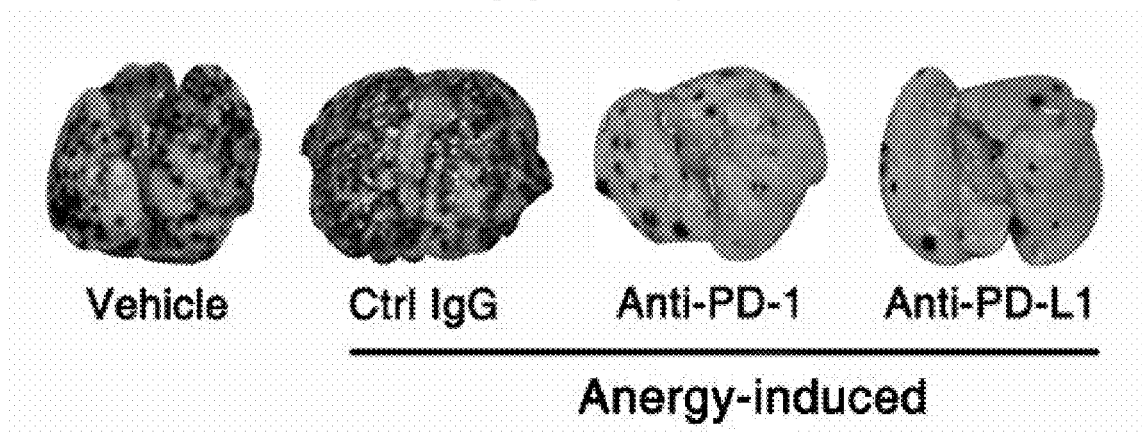

As seen in FIG. 10, when induced by treatment with the control IgG and α-GC, iNKT cell anergy was unchanged with time to show a metastasis result comparable to that of the normal metastasis control group, indicating that α-GC treatment during tumor inoculation did not suppress tumor growth. In contrast, when the anergy induction of α-GC was prevented by treatment with the anti-PD-1 antibody or the anti-PD-L1, the numbers of tumor nodules in the B16F10 melanoma metastasis model were remarkably reduced compared with those upon treatment with the control IgG, demonstrating the superior anti-tumor activity of the antibodies of the present invention. Taken together, the data obtained above indicates that the blockage of PD-1/PD-L1 interaction by treatment with the anti-PD-1 antibody or the anti-PD-L1 antibody during the induction phase of iNKT cell anergy leads to the persistence of the anti-tumor effects of iNKT cells.

Formulation examples are given to illustrate dosage preparations containing the anticancer agent of the present invention.

Formulation Example 1

Preparation of Powder

TABLE US-00001

Anti-PD-1 or Anti-PD-L1 Antibody 0.1 g Lactose 1.5 g Talc 0.5 g

These ingredients were mixed and loaded into an airtight sac to give a powder.

Formulation Example 2

Preparation of Tablet

TABLE US-00002

Anti-PD-1 or Anti-PD-L1 Antibody 0.1 g Lactose 7.9 g Crystalline cellulose 1.5 g Magnesium stearate 0.5 g These ingredients were mixed and directly compressed into a tablet.

Formulation Example 3

Preparation of Capsule

TABLE US-00003

Anti-PD-1 or Anti-PD-L1 Antibody 0.1 g Corn starch 5 g Carboxycellulose 4.9 g

These ingredients were admixed together and the admixture was loaded into a conventional capsule using a suitable device.

Formulation Example 4

Preparation of Injection

TABLE US-00004

Anti-PD-1 or Anti-PD-L1 Antibody 0.1 g Sterile water for injection proper quantity pH Adjuster proper quantity Using a conventional method, these ingredients were put into an ampule (2 ml) to give an injection.

Formulation Example 5

Preparation of Liquid Medicine

TABLE US-00005

Anti-PD-1 or Anti-PD-L1 Antibody 0.1 g Isomerized sugar 10 g Mannitol 5 g Purified water proper quantity Each ingredient was dissolved in purified water and flavored with lemon before admixing together. Purified water was added to the admixture to form a final volume of 100 ml which was then loaded into a brown vial and sterilized.

As described hitherto, the anti-PD-1 or anti-PD-L1 antibody according to the present invention blocks the PD-1/PD-L1-mediated signaling pathway not only to prevent the iNKT cell ligand-induced iNKT cell anergy, but also to reverse the unresponsiveness of already anergic iNKT cells to produce cytokines. In addition, the anti-PD1 or anti-PD-L1 antibody ensures the potent anti-tumor activity of iNKT cells as demonstrated by a significant reduction in the number of metastatic nodules in B16F10 melanoma metastasis models in vivo. Collectively, the anticancer agent comprising an anti-PD-1 or anti-PD-L1 antibody in accordance with the present invention can be very useful in the treatment of cancer, particularly metastatic cancer.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. An anticancer agent, comprising a first anticancer factor selected from a group consisting of alpha-galactosyl ceramide, alpha glucuronosyl ceramide, phosphatidylinositoltetramannoside, isoglobotrihexosylceramide, ganglioside GD3, phosphatidylcholine, phosphatidylethanolamine, phosphatidylinositol, sulfatide, beta-galactosylceramide, lipophoglycan, glycoinositol phospholipid, alphagalactosylceramide analogs including beta-anomer galactoceramide and alpha-anomer galactosylceramide, and combinations thereof, and a second anticancer factor selected from the group consisting of anti-PD-1 antibody and anti-PD-L1 antibody, having a function of reversing unresponsiveness of iNKT cells in which anergy is induced by administration with an iNKT cell ligand.

2. The anticancer agent as defined by claim 1, wherein the anti-PD-1 antibody or the anti-PD-L1 antibody is a monoclonal antibody or a polyclonal antibody.

3. The anticancer agent as defined by claim 1, wherein the cancer is selected from a group consisting of lung cancer, stomach cancer, liver cancer, bone cancer, pancreatic cancer, skin cancer, head and neck cancer, melanoma, uterine cancer, ovarian cancer, rectal cancer, colorectal cancer, colon cancer, breast cancer, uterine sarcoma, Fallopian tube carcinoma, endometrial carcinoma, uterine cervical carcinoma, vaginal carcinoma, vulva carcinoma, esophageal cancer, larynx cancer, small intestine cancer, thyroid cancer, parathyroid cancer, soft tissue sarcoma, uterine cancer, penis cancer, prostate cancer, chronic or acute leukemia, pediatric solid tumor, differentiated lymphoma, bladder cancer, kidney cancer, renal cell carcinoma, renal pelvic carcinoma, primary CNS lymphoma, spinal cord tumor, brainstem glioma, and pituitary adenoma.

4. The anticancer agent as defined in claim 1, wherein the first anticancer factor is alpha-galactosyl ceramide.

5. The anticancer agent as defined in claim 1, wherein the first anticancer factor is selected from the group consisting of alpha-galactosyl ceramide, alpha glucuronosyl ceramide, phosphatidylinositoltetramannoside, isoglobotrihexosylceramide, ganglioside GD3, sulfatide, beta-galactosylceramide, lipophophoglycan, glycoinositol phospholipid, alphagalactosylceramide analogs including beta-anomer galactoceramide and alpha-anomer galactosylceramide.

* * * * *